(12) United States Patent
Okawa et al.

(10) Patent No.: US 6,222,065 B1
(45) Date of Patent: Apr. 24, 2001

(54) PROCESS FOR THE PRODUCTION OF 1,5-NAPHTYLENEDIISOCYANATE

(75) Inventors: Yutaka Okawa; Tomoo Tsujimoto; Yutaka Kanbara; Hiroshi Matsunaga, all of Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 09/614,177

(22) Filed: Jul. 11, 2000

(30) Foreign Application Priority Data

Jul. 15, 1999 (JP) .................................................. 11-202248

(51) Int. Cl.$^7$ ................................................. C07C 263/00
(52) U.S. Cl. ............................................................. 560/338
(58) Field of Search ............................................... 560/338

(56) References Cited

U.S. PATENT DOCUMENTS 5,319,133 * 6/1994 Raynor et al. ........................ 560/338

* cited by examiner

*Primary Examiner*—Joseph K. McKane
*Assistant Examiner*—Joseph Murray
(74) *Attorney, Agent, or Firm*—Wenderoth, Lind & Ponack, L.L.P.

(57) ABSTRACT

1,5-naphthylenediisocyanate is industrially advantageously produced at high yields by pyrolyzing methyl 1,5-naphthylenecarbamate synthesized by providing 1,5-naphthylenedinitrile as a raw material and carrying out amidation, chlorination and Hofmann rearrangement.

12 Claims, No Drawings

PROCESS FOR THE PRODUCTION OF 1,5-NAPHTYLENEDIISOCYANATE

BACKGROUND OF THE INVENTION

1. Field of the Invention

The present invention relates to a process for the production of 1,5-naphthylenediisocyanate. More specifically, it relates to a process for producing 1,5-naphthylenediisocyanate at high yields, with little by-products and without the necessity of handling substances poisonous to a human body except chlorine.

1,5-Naphthylenediisocyanate is useful as a raw material for producing a polyurethane elastomer excellent in heat resistance, weather resistance and durability against repeated bending.

2. Description of the Prior Art

The 1,5-naphthylenediisocyanate production method employed in present industry uses naphthalene as a raw material and employs reaction steps including mononitration, dinitration, reduction and phosgene formation.

However, the above method involves various problems. That is, although naphthalene as a starting material is available at a low cost, there are defects that the yield in each step is low and that a large amount of by-products (waste products) are formed. For example, in the dinitration step, 1,8-dinitronaphthalene which is an isomer of 1,5-dinitronaphthalene is formed in an amount 1.8 times the amount of 1,5-dinitronaphthalene. In view of environments and safety, further, the problem is that it is required to handle 1,5-dinitronaphthalene and 1,5-diaminonaphthalene which are intermediates having mutagen poisonous to a human body, and another problem is that it is required to use highly toxic phosgene as a side raw material. In view of product quality, a large amount of hydrolysable chlorine is contained in 1,5-naphthylenediisocyanate and has detrimental effects on the weathering properties and heat resistance of polyurethane products.

Further, a variety of methods have been proposed with regard to the production of aromatic carboxylic acid amides from aromatic nitriles.

For example, Org. Syn. Col. Vol. 2, 586–587 (1943) discloses a method of amidation of o-tolunitrile by using hydrogen peroxide. However, this method uses a large amount of hydrogen peroxide as a side raw material.

British Patents 1133013 and 1351530 describe a method of amidation of a nitrile compound in the presence of manganese dioxide as a catalyst. In this method, a large amount of the catalyst is required, and formed aromatic carboxylic acid amides precipitate as a crystal, so that there is caused a problem that the crystal blocks the active center of the catalyst.

U.S. Pat. No. 3,763,235 discloses a method of amidation of a nitrile compound with a lower aliphatic carboxylic acid in the presence of a metal salt. The method requires a large amount of the catalyst as well. Further, a precipitating crystal of aromatic carboxylic acid amides entraps the catalyst, and the problem is that the separation of these is difficult.

PCT International Publication WO90/09988 discloses a method of contacting aromatic nitriles to perboric acid alkali metal salt in a water-containing alcohol. In this process, expensive perboric acid alkali metal salt is required in a large molar amount, as large as 2.5 to 4 times the molar amount of the aromatic nitriles.

JP-A-6-116221 and JP-A-6-128204 disclose a method of amidation of aromatic nitriles in a water-containing alcohol in the presence of an inorganic strong base and a method of reacting aromatic nitriles with an alcohol in an inorganic strong base to synthesize an iminoether compound and then amidating it by adding water. These Publications include examples of 2,6-naphthylenedinitrile. These methods are industrially excellent in the use of a less expensive alkali metal hydroxide as a catalyst. When the present inventors applied these methods to 1,5-naphthylenedinitrile having lower reactivity than 2,6-naphthylenedinitrile, however, 1,5-naphthylenedicarboxylic acid amide was obtained only at low yields, and it was found that the reaction product contained a non-negligible amount of terephthalic acid formed as a by-product (see Comparative Example 1).

The above carboxylic acid is consumed or converted to a salt of the carboxylic acid with the inorganic strong base which is added to the reaction system. When an isocyanate compound is synthesized from a carboxylic acid amide containing a carboxylic acid or a salt of a carboxylic acid according to the present invention, an end product comes to contain the carboxylic acid or the salt of a carboxylic acid, and it is therefore required to separate the carboxylic acid amide and the carboxylic acid from each other.

As described above, the above conventional methods for producing aromatic carboxylic acid amides from aromatic dinitrils are not necessarily satisfactory from the viewpoint of industry, since there are involved problems in the use of the expensive side raw material and a large amount of the catalyst and a problem that a purification step is required since a large amount of the carboxylic acid is formed as a by-product.

Further, the following methods are disclosed as a method in which aromatic carboxylic acid amides are reacted with chlorine to form aromatic carboxylic acid-bis-N-chloroamides and the aromatic carboxylic acid-bis-N-chloroamides are reacted in Hofmann rearrangement in an alcohol to obtain aromatic carbamate esters.

JP-A-5-65259 discloses a method in which aromatic carboxylic acid amides are reacted with chlorine in methanol to obtain aromatic carboxylic acid-bis-N-chloroamide. JP-A-7-291910 discloses a method in which aromatic carboxylic acid amides are chlorinated by mixing them with a solvent in which chlorine is pre-dissolved, to obtain aromatic carboxylic acid-bis-N-chloroamide. JP-A-5-65266 discloses a method in which aromatic carboxylic acid-bis-N-chloroamides are reacted with an alcohol in the presence of an inorganic strong base to obtain aromatic carbamate esters.

JP-A-5-65266 describes Example in which sodium hydroxide was added to, and mixed with, methanol under atmospheric pressure, 2,6-naphthalenedicarboxylic acid-bis-N-chloroamide at 5° C. was added little by little over 30 minutes while retaining a temperature of 5 to 10° C., and then, the reaction solution was gradually temperature-increased and allowed to react under the reflux of methanol for 2 hours, followed by cooling, filtering, washing with water and drying, to give 2,6-bis(methoxycarbonylamino) naphthalene having a purity of 95.4% by weight at a yield of 94.8 mol %.

The present inventors applied the above method to 1,5-naphthalenedicarboxylic acid-bis-N-chloroamide and found the following. The yield of 1,5-bis(methoxycarbonylamino) naphthalene was 49.2%. That is, in the case of 1,5-bis (methoxycarbonylamino)naphthalene, no high yield can be achieved unlike the high yield of 2,6-bis (methoxycarbonylamino)naphthalene (see Comparative Example 2).

There is also a method of pyrolysing aromatic carbamate esters to form isocyanates. This method includes a gas phase method and a liquid phase method, and the liquid phase method is advantageous in industry. The pyrolysis of carbamate esters undergoes in a reversible reaction, and its equilibrium shifts toward the formation of an isocyanate at a high temperature. The pyrolysis is generally therefore carried out at high temperatures. Since, however, the condition of the reaction is severe, an isocyanate causes various irreversible side reactions and easily form, for example, ureas, amides, carbodiimides, urethidiones and isocyanurates. These side reactions not only decrease the selectivity to isocyanates, but also cause the formation of by-products having high boiling points, so that it is made difficult to carry out continuous operation for a long period of time by the clogging of a reactor and tubings. For overcoming these problems, there have been proposed a method of using a catalyst or a solvent, a method of withdrawing a formed isocyanate from a reaction system in a short period of time by reaction distillation, and the like.

As a general method of pyrolyzing carbamate ester, for example, JP-B-57-45736 discloses method using a catalyst prepared by dissolving one or more metals selected from the group consisting of metal atoms belonging to the groups IB, IIB, IIIA, IVA, IVB, VB and VIII of the periodic table or compound(s) thereof in a solvent. JP-A-54-88201 discloses a method using an alkaline earth metal and an inorganic compound thereof as catalysts. JP-A-57-158747 discloses a method using one or more simple substances or compounds selected from the class consisting of element simple substances belonging to the copper group, the aluminum group, the carbon group excluding carbon and the titanium group of the periodic table and oxides or sulfides of these, as a heterogenous catalyst in a solvent. JP-A-7-258194 discloses a method using organic sulfonic acid and an alkali metal salt thereof as catalysts in a solvent.

For obtaining isocyanates at high yields by preventing the formation of by-products in the pyrolysis of carbamate esters, there are also proposed methods using stabilizers. For example, JP-A-57-123159 discloses a method using carboxylic acid chloride, sulfonate ester and an alkylating agent. JP-A-1-125359 discloses a method using phosphorous triester. JP-A-9-87239 discloses a method using aromatic sulfonic acids or aromatic sulfone amides.

Various methods are also proposed for the pyrolysis of bis(alkoxycarbonylamino)naphthalene. JP-A-56-65857 describes Example in which a tubular reactor packed with zinc chips was provided, and 1,5-bis(ethoxycarbonylamino) naphthalene was pyrolyzed under reduced pressure at 350° C., to give 1,5-naphthylenediisocyanate at a yield of 80.5%. JP-A-2-295958 describes Example in which 1,5-bis (ethoxycarbonylamino)naphthalene was pyrolyzed in the co-presence of a sulfolane solvent and a dibutyltin dilaurate catalyst under atmospheric pressure at a temperature of 200° C. for 5 hours, to give 1,5-naphthylenediisocyanate at a yield of 80.6%.

JP-A-11-5773 describes Example in which 2,6-bis (methoxycarbonylamino)naphthalene was pyrolyzed in two reaction solvents and one collecting solvent in the co-presence of a dibutyltin dilaurate catalyst and p-toluenesulfonic acid as a stabilizer under reduced pressure at 250° C., to obtain 2,6-naphthylenediisocyanate at a yield of 93.5%. When the present inventors applied this method to the production of 1,5-naphthylenediisocyanate, the yield of the 1,5-naphthylenediisocyanate was 63.9%, and it has been found that 1,5-bis(methoxycarbonylamino)naphthalene is less reactive than 2,6-bis(methoxycarbonylamino) naphthalene, so that no high yield can be attained.

As described above, when 1,5-bis(alkoxycarbonylamino) naphthalene is pyrolyzed according to any conventional method, the yield of 1,5-naphthylenediisocyanate is 81% or less, which is not at all satisfactory in industry.

As explained above, the existing methods of producing 1,5-naphthylenediisocyanate involves various problems, and it is desired to develop a new process.

SUMMARY OF THE INVENTION

It is an object of the present invention to provide a process for industrially advantageously producing 1,5-naphthylenediisocyanate from 1,5-naphthylenedinitrile at high yields.

According to the present invention, there is provided a process for the production of 1,5-naphthylenediisocyanate, comprising the first reaction step of amidating 1,5-naphthylenedinitrile in water-containing dimethylsulfoxide in the presence of an inorganic strong base, to prepare 1,5-naphthylenedicarboxylic acid amide, the second reaction step of reacting the 1,5-naphthylenedicarboxylic acid amide with chlorine in a solvent, to prepare 1,5-naphthylenedicarboxylic acid-bis-N-chloroamide, the third reaction step of reacting the 1,5-naphthylenedicarboxylic acid-bis-N-chloroamide with an alcohol in the presence of a basic compound, to prepare 1,5-bis(alkoxycarbonylamino)naphthalene, and the fourth reaction step of pyrolyzing 1,5-bis (alkoxycarbonylamino)naphthalene in an inert solvent to obtain 1,5-naphthylenediisocyanate.

DETAILED DESCRIPTION OF THE INVENTION

The present inventors have made diligent studies with regard to the process for the production of 1,5-naphthylenediisocyanate having the above problems. As a result, it has been found that 1,5-naphthylenediisocyanate can be industrially advantageously produced by using 1,5-naphthylenedinitrile as a raw material, carrying out amidation, chlorination and Hofmann rearrangement to prepare 1,5-bis(alkoxycarbonylamino)naphthalene, and pyrolyzing it. The conventional methods have a particular problem in the low yields in the amidation step. However, it has been found that 1,5-naphthylenecarboxylic acid amide can be obtained at high yields by reacting 1,5-naphthylenedinitrile with water in the presence of an inorganic strong base and dimethylsulfoxide, and some other advantages have been also found, so that the present invention has been accordingly completed.

The method of preparing 1,5-naphthylenedinitrile for use as a raw material in the process of the present invention is not critical. However, there is 1,5-naphthylenedimethyl that is industrially produced as an intermediate in the process of producing dimethyl 2,6-naphthylenedicarboxylate, and 1,5-naphthylenedinitrile can be prepared by ammoxidizing the 1,5-naphthylenedimethyl. For example, 1,5-naphthylenedinitrile can be easily obtained by providing a fluidized bed reactor packed with vanadium-chromium-boron-silica-supporting catalyst and reacting 1,5-naphthylenedimethyl, ammonia and air at a temperature between 430° C. and 450° C.

The first reaction step of amidation of 1,5-naphthylenedinitrile uses an inorganic strong base. The inorganic strong base generally includes alkali metal hydroxides such as sodium hydroxide and potassium hydroxide and alkali metal alkoxides such as sodium methoxide and potassium ethoxide. Industrially, sodium hydroxide available at a low price is preferred. The amount of the inorganic strong base per mole of the 1,5-naphthylenedinitrile is preferably in the range of from 0.01 to 1 mol. When the amount of the inorganic strong base is smaller than the above lower limit, the reaction rate is low, so that the yield of 1,5-naphthylenedicarboxylic acid amide from the 1,5-naphthylenedinitrile is low. When the above amount is larger than the above upper limit, the reaction rate&is high, while such a large amount is not economical.

In the first reaction step, 1,5-naphthylenedinitrile is amidated in water-containing dimethylsulfoxide, whereby 1,5-naphthylenedicarboxylic acid amide can be obtained at high yields. The amount of the water per mole of 1,5-naphthylenedinitrile is preferably in the range of from 1.5 to 50 mol. When the amount of the water is smaller than the above lower limit, the amidation of the 1,5-naphthylenedinitrile is not completed. When the above amount of the water is larger than the above upper limit, 1,5-naphthylenedicarboxylic acid is formed as a by-product. In any case of these, therefore, the yield of the 1,5-naphthylenedicarboxylic acid amide is low.

1,5-Naphthylenedinitrile used as a raw material is soluble in water-containing dimethylsulfoxide under reaction conditions, and then 1,5-naphthylenedicarboxylic acid amide precipitates as a crystal. The amount of the water-containing dimethylsulfoxide is preferably adjusted such that the concentration of the 1,5-naphthylenedinitrile charged is in the range of from 1 to 50% by weight. When the amount of the water-containing dimethylsulfoxide is smaller than the amount which can attain the above upper limit, it is difficult to stir a reaction system. When the above amount is larger than the amount which can attain the above lower limit, uneconomically, the space time yield is low.

The reaction temperature in the first reaction step is between 50° C. and 150° C. When the reaction temperature is higher than the above upper limit, formed 1,5-naphthylenedicarboxylic acid amide is hydrolyzed, to increase the amount of 1,5-naphthylenedicarboxylic acid formed as a by-product. When the reaction temperature is lower than the above lower limit, the reaction rate is low. The reaction time period differs depending upon the kind and amount of the inorganic strong base, charging conditions of the water and dimethylsulfoxide and the reaction temperature and cannot be uniformly determined. Generally, the reaction time period is 0.5 to 10 hours, preferably 0.5 to 5 hours.

The 1,5-naphthylenedicarboxylic acid amide formed in the first reaction step is cooled and filtered, whereby can be easily isolated and recovered. A filtrate contains a small amount of unreacted 1,5-naphthylenedinitrile and a small amount of 1,5-naphthylenedicarboxylic acid amide. However, the filtrate may be recycled to the reaction system for improving the use efficiency of the catalyst and the yield from the reaction.

The chlorination of the 1,5-naphthylenedicarboxylic acid amide in the second reaction step is carried out in a solvent. Specifically, the solvent can be selected from water, methanol or N,N'-dimethylformamide. These solvents may be used alone or in combination. During the reaction, 1,5-naphthylenedicarboxylic acid amide and formed 1,5-naphthylenedicarboxylic acid-bis-N-chloroamide are present in crystal states. The amount of the solvent is therefore determined to be in such an amount range that the reaction system can be stirred. Generally, the solvent is used in such an amount that the reaction solution has a 1,5-naphthylenedicarboxylic acid amide concentration of 2 to 30% by weight. When the amount of the solvent is smaller than an amount at which the above upper limit of the 1,5-naphthylenedicarboxylic acid amide concentration can be retained, it is difficult to stir the reaction system. When it is larger than an amount at which the above lower limit of the 1,5-naphthylenedicarboxylic acid amide concentration can be retained, the space time yield is low, which is uneconomical.

The amount of chlorine for use per mole of 1,5-naphthylenedicarboxylic acid amide in the second reaction step is preferably in the range of from 2 to 30 mol. When the amount of chlorine is smaller than the above lower limit, the reaction rate is low, and the amount of unreacted 1,5-naphthylenedicarboxylic acid amide is increased. When the above amount is larger than the above upper limit, the space time yield is low, which is uneconomical.

The reaction temperature in the second reaction step is in the range of from 0 to 50° C. When the reaction temperature is higher than the above upper limit, 1,5-naphthylenedicarboxylic acid-bis-N-chloroamide is decomposed to decrease the yield. When the reaction temperature is lower than the above lower limit, the reaction rate is low. The reaction time period differs depending upon charging conditions and the reaction temperature, while it is generally 0.5 to 5 hours.

The reaction method between 1,5-naphthylenedicarboxylic acid amide and chlorine is not critical, and it can be carried out by a variety of methods. For example, in one method, 1,5-naphthylenedicarboxylic acid amide is suspended in a solvent in a reactor, and while the suspension is stirred, chlorine gas is continuously fed at a reaction temperature to carry out the reaction. In another method, chlorine is dissolved in a solvent in a reactor in advance, 1,5-naphthylenedicarboxylic acid amide is added, the mixture is stirred, and while chlorine gas is further continuously fed, the reaction is carried out at a given temperature.

A crystal of 1,5-naphthylenedicarboxylic acid bis-N-chloroamide formed by the reaction can be easily isolated and recovered by filtering. On the other hand, a filtrate contains a small amount of unreacted 1,5-naphthylenedicarboxylic acid amide and a small amount of 1,5-naphthylenedicarboxylic acid-bis-N-chloroamide, and the filtrate may be recycled to the reaction system after dissolved chlorine and hydrogen chloride formed as a by-product are removed.

In the third reaction step, the 1,5-naphthylenedicarboxylic acid-bis-N-chloroamide is reacted with an alcohol in the presence of a basic compound, to form 1,5-bis (alkoxycarbonylamino)naphthalene. The basic compound can be selected from alkali metal hydroxides such as sodium hydroxide and potassium hydroxide, alkali metal alkoxides such as sodium methoxide and potassium ethoxide, amine-containing organic strong bases such as 1,8-diazabicyclo [5.4.0]-7-undecene and 1,4-diazabicyclo[2.2.2]octaneor a basic ion exchange resin. Industrially, sodium hydroxide available at a low price is particularly preferred.

The amount of the basic compound per mole of the 1,5-naphthylenedicarboxylic acid-bis-N-chloroamide is in the range of from 2 to 5 mol. When the amount of the basic compound is less than the above lower limit, the reaction does not proceed quantitatively. When the amount of the basic compound is larger than the above upper limit, it is disadvantageous in view of economic performance.

The alcohol used in the present invention is generally selected from linear or branched lower aliphatic alcohols having 1 to 4 carbon atoms. Specific examples of the alcohol include methanol, ethanol, n-propanol, isopropanol and tert-butanol. Methanol is particularly preferred for an economical reason.

The amount of the alcohol per mole of the 1,5-naphthylenedicarboxylic acid-bis-N-chloroamide is at least 2 mol. The 1,5-naphthylenedicarboxylic acid-bis-N-chloroamide and 1,5-bis(alkoxycarbonylamino)naphthalene are crystals. Therefore, when the amount of the alcohol is too small, it is difficult to stir the reaction system. Further, when the above amount is too large, it is economically disadvantageous. Generally, therefore, the alcohol is used in such an amount that the concentration of 1,5-naphthylenedicarboxylic acid-bis-N-chloroamide in the reaction system is 1 to 50% by weight.

In the Hofmann rearrangement of the 1,5-naphthylenedicarboxylic acid-bis-N-chloroamide in the third reaction step, generally, the hofmann rearrangement is carried out by the following method using methanol as the alcohol.

The 1,5-naphthylenedicarboxylic acid-bis-N-chloroamide is dissolved or suspended, for example, in methanol to prepare a solution or suspension, and while the solution or suspension is stirred, an inorganic strong base is added. Then, the mixture is temperature-increased up to a reaction temperature and maintained for a predetermined period of time. In another method, an inorganic strong base is dissolved or suspended in methanol to prepare a solution or suspension, the 1,5-naphthylenedicarboxylic acid-bis-N-chloroamide is added thereto, and then, the reaction is carried out as described above.

In the present invention, the third reaction step may be separated to a first step and a second step which are different in temperature range. The above separation is particularly preferred since 1,5-bis(methoxycarbonylamino)naphthalene can be obtained at high yields. The reaction temperature in the first step is in the range of from −20° C. to less than 10° C., preferably 10° C. to 5° C. In the first step, it is assumed that an intermediate is formed by Hofmann rearragnement and causes a side reaction. When the reaction temperature is higher than the above upper limit, it is therefore difficult to obtain 1,5-bis(methoxycarbonylamino)naphthalene at high yields. When the reaction temperature is too low, the reaction rate is too low.

The reaction time in the first step is generally 0.5 to 5 hours although it differs depending upon the concentration of 1,5-naphthylenedicarboxylic acid-bis-N-chloroamide and the reaction temperature.

The 1,5-naphthylenedicarboxylic acid-bis-N-chloroamide used as a starting material in the third reaction step is rarely dissolved in methanol. However, an intermediate changes to methanol-soluble in the reaction in the first step. The 1,5-bis(methoxycarbonylamino)naphthalene formed in the second step is rarely dissolved in methanol, so that it precipitates as a crystal in the reaction solution. When 1,5-naphthylenedicarboxylic acid amide is contained as an impurity in the starting material, it precipitates as a crystal in the reaction solution in the first step, so that it is preferred to filter the reaction mixture to separate the 1,5-naphthylenedicarboxylic acid amide off and use the filtrate alone for the reaction in the second step. After the above filtration is carried out, a crystal obtained by the filtration and separation of the reaction mixture in the second step contains no 1,5-naphthylenedicarboxylic acid amide, and high-purity 1,5-bis(methoxycarbonylamino)naphthalene can be obtained. On the other hand, in a method in which the filtration is carried out after the reaction in the second step as described in the already described reference, 1,5-naphthylenedicarboxylic acid amide, if contained in the starting material, remains in the 1,5-bis(methoxycarbonylamino)naphthalene separated by filtration, so that the 1,5-bis(methoxycarbonylamino)naphthalene comes to have a poor purity.

The temperature in the second step is in the range of from 10 to 50° C., preferably from 15 to 40° C. In the second step, an intermediate formed in the first step further undergoes a reaction, and 1,5-bis(methoxycarbonylamino)naphthalene precipitates, so that the reaction mixture gradually comes to be opaque. When the reaction temperature in the second step is too low, the reaction rate is low. When this reaction temperature is too high, a by-product is formed, and the yield is low.

The reaction time period in the second step is generally in the range of from 0.1 to 10 hours although it differs depending upon the concentration of the 1,5-naphthylenedicarboxylic acid-bis-N-chloroamide and the reaction temperature. Generally, the 1,5-bis(methoxycarbonylamino)naphthalene can be isolated and recovered from the reaction mixture in the second step by filtration and washing with water or an alcohol after the mixture is cooled.

In the present invention, the first step and the second step are carried out generally under atmospheric pressure, although the pressure in each step is not critical. The process of the present invention can be carried out by a batch method or a continuous method. The 1,5-naphthalenedicarboxylic acid amide obtained as a crystal by filtration in the first step can be recycled as a raw material for the synthesis of the 1,5-naphthylenedicarboxylic acid-bis-N-chloroamide. The filtrate resulting from the filtration after the second step contains a small amount of 1,5-bis(methoxycarbonylamino) naphthalene in an alcohol, so that it can be also recycled as required.

The pyrolysis of the 1,5-bis(alkoxycarbonylamino) naphthalene in the fourth reaction step may be carried out in an inert solvent even in the absence of a catalyst. However, it is preferred to use a catalyst such as metal cobalt or a cobalt compound. For example, the cobalt compound can be selected from inorganic and organic acid salts, complexes, oxides and sulfides such as cobalt phosphate, cobalt sulfate, cobalt iodide, cobalt choride, cobalt acetate, cobalt benzoate, cobalt acetyl acetonate, cobalt naphthenate, cobalt stearate, cobalt oxide, cobaltocene, cobalt sulfide, and the like. Cobalt acetate is particularly preferred.

The inert solvent in the fourth reaction step includes hydrocarbon compounds having high boiling points. Dibenzyltoluene is particularly preferred. Dibenzyltoluene has a higher boiling point than 1,5-bis(alkoxycarbonylamino) naphthalene, so that 1,5-bis(alkoxycarbonylamino) naphthalene can be pyrolyzed by maintaining the solvent in a boiling state in the form of reaction distillation, i.e., at a reaction temperature, and at the same time, formed 1,5-naphthylenediisocyanate can be distilled out of the system. In this manner, there is brought an advantage that the concentration of 1,5-naphthylenediisocyanate in the reaction system can be maintained at a low level, and that a side reaction caused by an unstable isocyanate compound can be inhibited.

The amount of the inert solvent is 0.05 to 20 times, preferably 0.1 to 10 times, the weight of the 1,5-bis (alkoxycarbonylamino)naphthalene. When the amount of the inert solvent is smaller than the above lower limit, a side reaction increases. When it is greater than the above upper limit, it is uneconomical since the space time yield is low.

The amount of the catalyst as a concentration thereof in a solvent is in the range of 0.00001 to 10% by weight, preferably 0.0001 to 1% by weight. When the concentration of the catalyst is lower than the above lower limit, the reaction rate is low. When it is higher than the above upper limit, a side reaction increases, and the yield is low.

As a stabilizer for inhibiting a side reaction in the fourth reaction step, it is preferred to use aromatic sulfonic acid. Specific examples of the aromatic sulfonic acid include benzenesulfonic acid, ethylbenzenesulfonic acid, toluenesulfonic acid, xylenesulfonic acid, naphthalenesulfonic acid, phenolsulfonic acid and sulfanilic acid. These stabilizers may be used alone or in combination. The stabilizer is continuously or intermittently fed to a required portion in a reactor, whereby the side reaction such as polymerization can be inhibited. The amount of the stabilizer as a concentration thereof in a solvent is in the range of from 0.0001 to 10% by weight, preferably 0.001 to 1% by weight. When the concentration of the stabilizer is lower than the above lower limit, the effect on inhibiting the side reaction is low. When it is higher than the above upper limit, the reaction rate is decreased.

The 1,5-bis(alkoxycarbonylamino)naphthalene is pyrolyzed at a temperature between 150° C. and 300° C., preferably between 200° C. and 300° C. When the reaction temperature is lower than the above lower limit, the reaction rate is low. When it is higher than the above upper limit, a side reaction increases, and the yield is low. The reaction is generally carried out under reduced pressure, while it may be also carried out under atmospheric pressure or under elevated pressure. The reaction time period is generally 0.2 to 5 hours, although it differs depending upon the reaction temperature, the pressure, a reaction method, and the like.

Under the above-described reaction conditions, 1,5-bis (alkoxycarbonylamino)naphthalene is pyrolyzed into 1,5-naphthylenediisocyanate and an alcohol. However, these are easily recombined to recover 1,5-bis(alkoxycarbonylamino) naphthalene, so that these compounds are generally separately recovered. The method of the recovery includes, for example, a method in which a vapor of 1,5-naphthylenediisocyanate and an alcohol is withdrawn from the reaction system and each is separately condensed by utilizing a difference in condensation temperature and a method in which only an alcohol having a low boiling point is withdrawn from the reaction system.

While the pyrolysis of the 1,5-bis(alkoxycarbonylamino) naphthalene may be carried out by a batch method, it is practical to carry out the pyrolysis by a continuous method using a complete mixing type reactor or a tubular reactor. The continuous method can be preferably carried out as follows. For example, a multi-stage distillation column is used as a reactor for the pyrolysis. A raw material solution containing 1,5- bis(alkoxycarbonylamino)naphthalene, a solvent, a catalyst and a stabilizer is continuously fed into the reactor or a middle stage of the column maintained at a predetermined temperature under reduced pressure, 1,5-naphthylenediisocyanate and an alcohol formed by the reaction are separately condensed outside the system. The so-obtained 1,5-naphthylenediisocyanate fraction is further distilled and recrystallized as required, whereby it is obtained as a high-purity product. On the other hand, a residue is continuously or intermittently withdrawn prom the reactor, by-products having high boiling points are removed with an evaporator, and effective components containing unreacted 1,5-bis(alkoxycarbonylamino)naphthalene and 1,5-naphthylenemono- and di-isocyanate are recycled to the reaction system.

In the process of the present invention, each reaction step can be carried out by a batch method or a continuous method, so that a production process can be constructed by combining these steps. In each reaction step, high yields can be attained under the above-described reaction conditions and procedures. Further, it has been confirmed that 1,5-naphthylenedicarboxylic acid amide, 1,5-naphthylenedicarboxylic acid-bis-N-chloroamide and 1,5-bis(alkoxycarbonylamino)naphthalene as intermediates do not have toxicity to human bodies such as mutagen.

According to the present invention, there is provided a process which enables the production of 1,5-naphthylenedicarboxylic acid amide at high yields almost without causing the formation of 1,5-naphthylenedicarboxylic acid as a by-product by reacting 1,5-naphthylenedinitrile and water in the presence of an inorganic strong base and dimethylsulfoxde. According to the present invention, there can be produced a high-purity aromatic dicarboxylic acid amide without using any expensive side raw material or any expensive catalyst.

According to the present invention, further, there is provided a process which enables the production of high-purity 1,5-bis(alkoxycarbonylamino)naphthalene at high yields from 1,5-naphthylenedicarboxylic acid-bis-N-chloroamide. According to the present invention, 1,5-bis (alkoxycarbonylamino)naphthalene can be easily produced at high yields, which production has been hitherto difficult.

According to the present invention, further, the reaction rate is increased by using a cobalt compound as a catalyst for the pyrolysis of 1,5-bis(alkoxycarbonylamino)naphthalene, and there is provided a process which enables the production of 1,5-naphthylenediisocyanate at high yields. Further, by using an aromatic sulfonic acid as a stabilizer, the selectivity to 1,5-naphthylenediisocyanate is increased.

In the present invention, 1,5-naphthylenedinitrile is used as a raw material, the amidation, chlorination and Hofmann rearrangement are carried out, to synthesize methyl 1,5-bis (alkoxycarbonylamino)naphthalene, and the 1,5-bis (alkoxycarbonylamino)naphthalene is pyrolyzed, whereby 1,5-naphthylenediisocyanate can be produced at high yields.

According to the present invention, therefore, yields in each step are high as compared with those in conventional methods, so that the amount of by-products (waste products) is decreased, and substances poisonous to human bodies are not handled except chlorine, so that there can be provided a process for the production of 1,5-naphthylenediisocyanate, which process is excellent in view of environmental problems and safety.

EXAMPLES

The present invention will be explained more in detail with reference to Examples and Comparative Examples hereinafter, while the present invention shall not be limited to Examples.

Example 1

First Reaction Step

A one-liter three-necked flask equipped with a stirrer and a thermometer was charged with 44.5 g of 1,5- naphthylenedinitrile (purity: 99.13%), 500 g of dimethyl sulfoxide, 50 g of a 1N sodium hydroxide aqueous solution and 25 g of water. In this case, the molar ratio of the sodium hydroxide to the 1,5-naphthylenedinitrile was 0.20, and the molar ratio of the water thereto was 16.9. The flask was placed in an oil bath, and the mixture was temperature-increased up to 98° C. with stirring and maintained for 3 hours. During the above procedure, the reaction mixture formed a homogeneous solution when the temperature was increased up to a point over about 90° C., and then, it formed a slurry due to the formation of an amide and the precipitation of a crystal.

After completion of the reaction, the reaction solution was filtered and rinsed with water and a solid was dried to give 51.5 g of a white crystal. The crystal was analyzed by liquid chromatography to show that the content of 1,5-naphthylenedicarboxylic acid amide was 98.9%. The yield thereof based on the 1,5-naphthylenedinitrile as a raw material was 96.0%.

Example 2

First Reaction Step

In the same manner as in Example 1, a one-liter three-necked flask equipped with a stirrer and a thermometer was charged with 44.5 g of 1,5-naphthylenedinitrile (purity: 99.13%), 550 g of dimethylsulfoxide, 50 g of a 1N sodium hydroxide aqueous solution and 50 g of water, and these materials were allowed to react at a reaction temperature of 97° C. for 3 hours. In this case, the molar ratio of the sodium hydroxide to the 1,5-naphthylenedinitrile was 0.20, and the molar ratio of the water thereto was 22.5.

After completion of the reaction, the reaction solution was filtered and rinsed with water and a solid was dried to give 51.5 g of a white crystal. The crystal was analyzed by liquid chromatography to show that the content of 1,5-naphthylenedicarboxylic acid amide was 99.4%. The yield thereof based on the 1,5-naphthylenedinitrile as a raw material was 96.5%.

Example 3

First Reaction Step

In the same manner as in Example 1, a one-liter three-necked flask equipped with a stirrer and a thermometer was charged with 44.5 g of 1,5-naphthylenedinitrile (purity: 99.96%), 550 g of dimethylsulfoxide, 50 g of a 1N potassium hydroxide aqueous solution and 50 g of water, and these materials were allowed to react at a reaction temperature of 97° C. for 3 hours. In this case, the molar ratio of the potassium hydroxide to the 1,5-naphthylenedinitrile was 0.20, and the molar ratio of the water thereto was 22.5.

After completion of the reaction, the reaction solution was filtered and rinsed with water and a solid was dried to give 50.5 g of a white crystal. The crystal was analyzed by liquid chromatography to show that the content of 1,5-naphthylenedicarboxylic acid amide was 99.0%. The yield thereof based on the 1,5-naphthylenedinitrile as a raw material was 94.2%.

Comparative Example 1

First Reaction Step

A one-liter three-necked flask equipped with a stirrer and a thermometer was charged with 89.1 g of 1,5-naphthylenedinitrile (purity: 99.13%), 500 g of n-propanol and 50 g of 8 wt % sodium hydroxide aqueous solution. In this case, the molar ratio of the sodium hydroxide to the 1,5-naphthylenedinitrile was 0.20, and the molar ratio of water thereto was 5.1. The flask was placed in an oil bath, and the reaction temperature was increased up to 90° C. with stirring, and stirring was continued for 3 hours.

After completion of the reaction, the reaction solution was filtered and rinsed with water and a solid was dried to give 71 g of a white crystal. The crystal was analyzed by liquid chromatography to show that the content of 1,5-naphthylenedicarboxylic acid amide was 8.41% and that the rest was made of unreacted 1,5-naphthylenedinitrile. The yield thereof based on the 1,5-naphthylenedinitrile as a raw material was 5.6%.

Example 4

Second Reaction Step

A one-liter three-necked flask equipped with a stirrer, a thermometer and a chlorine-feeding nozzle was charged with 26 g of 1,5-naphthylenedicarboxylic acid amide (purity: 98.6%), 450 g of methanol and 150 g of water. The flask was placed in a constant-temperature water bath, and the temperature of the reaction mixture was maintained at 20° C. with stirring. Then, 28 g of chlorine was dissolved in the reaction solution through the chlorine-feeding nozzle, and then, chlorine gas was continuously fed into the reaction solution at a feed rate of 23.2 g per hour for 4 hours while measuring the chorine gas with a rotor meter.

After completion of the reaction, the chorine gas was switched to nitrogen, and nitrogen was blown into the reaction solution to purge chlorine and hydrogen chloride dissolved in the reaction solution from the system. Then, the reaction solution was cooled to 3° C., then filtered and rinsed with water, and a solid was dried to give 31.5 g of a white crystal. The crystal was analyzed by liquid chromatography to show that the content of 1,5-naphthylenedicarboxylic acid-bis-N-chloroamide was 98.1%. The yield thereof based on the 1,5-naphthylenedicarboxylic acid amide was 96.4%.

Example 5

Third Reaction Step

A two-liter three-necked flask equipped with a stirrer, a thermometer and a reflux condenser was charged with 30 g of 1,5-naphthylenedicarboxylic acid-bis-N-chloroamide (purity: 95.3%) and 750 g of methanol. The flask was placed in a constant-temperature water-methanol bath, and the reaction mixture was stirred and maintained at a temperature of 0° C. To the reaction mixture was added 10 g of sodium hydroxide, and the mixture was stirred for 1 hour. Then, the reaction mixture was filtered to remove an insoluble content. A filtrate was recycled to the flask placed in the water-methanol bath, and while the mixture in the flask was stirred, the reaction mixture was temperature-increased from 0° C. to 25° C. Then, the reaction mixture was stirred.

After completion of the reaction, the reaction solution was cooled to 0° C., filtered and rinsed with water, and a solid was dried to give 26 g of a white crystal. The crystal was analyzed by liquid chromatography to show that the content of 1,5-bis(methoxycarbonylamino)naphthalene was 99.3%. The yield thereof based on the 1,5-naphthylenedicarboxylic acid-bis-N-chloroamide as a raw material was 93.1%.

Example 6

Fourth Reaction Step

As a reactor, there was provided a 500-ml electromagnetic stirring autoclave having a packed column (packing agent:

Dixon Packing, number of stages: 8), a raw material feeding nozzle, a catalyst feeding nozzle, a reaction product withdrawing nozzle, a thermocouple protection tube and a hot medium circulating jacket. With the above autoclave, 1,5-bis(methoxycarbonylamino)naphthalene was pyrolyzed continuously. The reactor was all made of stainless steel (SUS-304). To a top of the packed column were connected a condenser, an air-cooling mist trap, a trap cooled with dry ice and methanol, a vacuum pump and a waste gas-vent through tubings. Hot medium oil at 140° C. was circulated in the condenser on the packed column top, and it was arranged that an isocyanate fraction formed by condensation therein was distilled out into a receiving container under a condition of a reflux ratio of 1.

At room temperature, a raw material vessel flushed with nitrogen gas was charged with 1,5-bis(methoxycarbonylamino)naphthalene and a dibenzyltoluene solvent having an amount 4 times the amount of the 1,5-bis(methoxycarbonylamino)naphthalene, and then cobalt acetate as a catalyst and p-toluenesulfonic acid as a stabilizer were added in an amount of 800 ppm each based on the solvent. Then, while a very small amount of nitrogen gas was introduced, the mixture was stirred to prepare a raw material solution. A reactor was charged with 250 g of dibenzyltoluene solvent, and while the solvent was stirred, the solvent was adjusted to a temperature of 250° C. and the pressure in the reactor was adjusted to 20 mmHg. The raw material solution was continuously fed to the reactor with a quantitative pump at a rate of 250 g/hour. 1,5-Naphthylenediisocyanate formed by the reaction was collected into the receiving container at a reflux ratio of 1, and methanol was collected into the cold trap. In the reactor, a residue liquid was continuously withdrawn into a receiving container with an electromagnetic valve linked with a liquid surface meter such that the liquid level was maintained at 250 g.

After initiation of the reaction, the reaction was continued for 10 hours. During this procedure, liquids in each receiving container and the cold trap were measured for amounts, and each liquid was analyzed for a composition with a liquid chromatograph and a gas chromatograph to carry out reaction analysis. As a result, in a steady state, the conversion of the 1,5-bis(methoxycarbonylamino)naphthalene was 97.7%, the selectivity to the 1,5-naphthylenediisocyanate was 92.6%, and the selectivity to a monoisocyanate as an intermediate was 3.9%.

What is claimed is:

1. A process for the production of 1,5-naphthylenediisocyanate, comprising the first reaction step of amidating 1,5-naphthylenedinitrile in water-containing dimethylsulfoxide in the presence of an inorganic strong base, to prepare 1,5-naphthylenedicarboxylic acid amide, the second reaction step of reacting the 1,5-naphthylenedicarboxylic acid amide with chlorine in a solvent, to prepare 1,5-naphthylenedicarboxylic acid-bis-N-chloroamide, the third reaction step of reacting the 1,5-naphthylenedicarboxylic acid-bis-N-chloroamide with an alcohol in the presence of a basic compound, to prepare 1,5-bis(alkoxycarbonylamino)naphthalene, and the fourth reaction step of pyrolyzing 1,5-bis(alkoxycarbonylamino)naphthalene in an inert solvent to obtain 1,5-naphthylenediisocyanate.

2. A process according to claim 1, wherein the inorganic strong base used in the first reaction step is sodium hydroxide.

3. A process according to claim 1, wherein the solvent used in the second reaction step is at least one member selected from the group consisting of water, methanol and N,N-dimethylformamide.

4. A process according to claim 1, wherein the basic compound used in the third reaction step is alkali metal hydroxide, alkali metal alkoxide, an amine-containing organic strong base or a basic ion-exchange resin.

5. A process according to claim 4, wherein the basic compound is sodium hydroxide.

6. A process according to claim 1, wherein the alcohol used in the third reaction step is a linear or branched aliphatic alcohol having 1 to 4 carbon atoms.

7. A process according to claim 6, wherein the alcohol is methanol.

8. A process according to claim 1, wherein the inert solvent used in the fourth reaction step is dibenzyltoluene.

9. A process according to claim 1, wherein the pyrolysis in the fourth reaction step uses cobalt metal or a cobalt compound as a catalyst.

10. A process according to claim 9, wherein the cobalt compound is at least one member selected from the group consisting of inorganic acid salts, organic acid salts, complexes, oxide and sulfides of cobalt.

11. A process according to claim 1, wherein the pyrolysis in the fourth step uses an aromatic sulfonic acid as a stabilizer.

12. A process according to claim 1, wherein the pyrolysis in the fourth step is carried out at a temperature between 150° C. and 350° C.

* * * * *

UNITED STATES PATENT AND TRADEMARK OFFICE
CERTIFICATE OF CORRECTION

PATENT NO. : 6,222,065 B1
DATED : April 24, 2001
INVENTOR(S) : Takashi Okawa et al.

It is certified that error appears in the above-identified patent and that said Letters Patent is hereby corrected as shown below:

<u>Title page,</u>
The first listed inventor's first name should be changed from "Yutaka" to -- Takashi --.

Signed and Sealed this

Eighteenth Day of September, 2001

*Attest:*

*Attesting Officer*

NICHOLAS P. GODICI
*Acting Director of the United States Patent and Trademark Office*